United States Patent [19]
Brown et al.

[11] Patent Number: 5,739,001
[45] Date of Patent: Apr. 14, 1998

[54] SOLID PHASE CELL-BASED ASSAY

[75] Inventors: Beverly Ann Brown, Winchester, Mass.; Patricia Ann Kasila, Windham, N.H.

[73] Assignee: E. I. du Pont de Nemours and Company, Wilmington, Del.

[21] Appl. No.: 744,718

[22] Filed: Oct. 29, 1996

[51] Int. Cl.$^6$ .................. G01N 33/543; C12Q 1/68
[52] U.S. Cl. .................. 435/7.93; 435/6; 436/518
[58] Field of Search .................. 435/6, 7.1, 7.21, 435/7.9, 7.92, 7.93, 7.94, 40.51, 70.1; 436/543, 544, 545, 546, 822, 518

[56] References Cited

U.S. PATENT DOCUMENTS

| | | | |
|---|---|---|---|
| 4,000,252 | 12/1976 | Kosak | 424/1 |
| 4,568,649 | 2/1986 | Bertoglio-Matte | 436/534 |
| 4,626,513 | 12/1986 | Burton et al. | 436/518 |
| 5,128,270 | 7/1992 | Delacroix et al. | 436/518 |

FOREIGN PATENT DOCUMENTS

| | | |
|---|---|---|
| 0 106 662 B2 | 4/1984 | European Pat. Off. |
| 0 378059 A1 | 7/1990 | European Pat. Off. |
| 0 438 470 B1 | 7/1991 | European Pat. Off. |
| 90/03844 | 4/1990 | WIPO |
| 94/26413 | 11/1994 | WIPO |

OTHER PUBLICATIONS

Sun et al., T and B cell responses to myelin–oligodendrocyte glycoprotein in multiple sclerosis. J. Immunol. 146(5):1490–1495, 1991.

Stephen R. Adams et al., Fluorescence ratio imaging of cyclic AMP in single cells, *Nature*, 349, 694–697, Feb. 21, 1991.

G. A. Langer et al., Calcium Exchange in a Single Layer of Rat Cardiac Cells Studied by Direct Counting of Cellular Activity of Labeled Calcium, *Circulation Research*, 24, No. 5, 589–597, May 1969.

Cecil C. Czerkinsky, Antigen–secreting Cells, *Methods of Enzymatic Analysis*, Bergemeyer, HU, Editor–in–Chief, 10, 11–22, 1986.

J. S. Frank, et al., The Myocardial Cell Surface, Its Histochemistry, and the Effect of Sialic Acid and Calcium Removal on Its Structure and Cellular Ionic Exchange, *Circulation Research*, 41, No. 5, 702–714, Nov. 1977.

*Primary Examiner*—Marian C. Knode
*Assistant Examiner*—Donna C. Wortman

[57] ABSTRACT

A solid phase cell-based assay is described which can be used to study cellular and biochemical processes in living cells which are responding to a stimulus by evaluating cell-related analytes without the need to attach the cell to the solid phase, without the need to radioactively label the cell either by incorporating a radioactive label into the cell or introducing a radioactive label onto the cell surface and without the need to employ cell culture techniques.

4 Claims, No Drawings

SOLID PHASE CELL-BASED ASSAY

FIELD OF THE INVENTION

This invention relates to a solid phase assay and, in particular, to a solid phase cell-based assay to study cellular and biochemical processes in living cells which are responding to a stimulus by evaluating cell-related analytes without the need to attach the cell to the solid phase, without the need to radioactively label the cell either by incorporating a radioactive label into the cell or introducing a radioactive label onto the cell surface and without the need to employ cell culture techniques.

BACKGROUND OF THE INVENTION

Cells are found in an enormous variety of sizes and shapes representing their evolutionary adaptation to different environments or to different specialized functions within a multicellular organism. Cells range in size from the smallest bacteria, only a few tenths of a micrometer in diameter, to certain marine algae and to various bird eggs with dimensions of centimeters.

For all their apparent diversity, however, cells have many characteristics in common, the most basic of which is the potential for an independent existence. That is, cells have the ability to continue living in the absence of any other cell, a capacity that requires fsst, a metabolic machinery capable of obtaining energy from the environment through capture of light or the degradation of chemical foodstuff, and second, the ability to use this energy to support essential life processes. These processes include the movement of components from one part of the cell to another, the selective transfer of molecules into and out of the cell, and the ability to transform molecules from one chemical configuration to another in order to replace parts as they wear out to support growth and reproduction. In addition to this metabolic machinery, a cell must have a set of genes to act as blueprints for the synthesis of other components. And finally, a cell must have a physical delimiter, a boundary between it and the rest of the world, callled the cell membrane.

Cells of all types can be maintained, i.e., "cultured," in a laboratory, although not all specialized cells can be made to reproduce. Growth may take place in liquid suspension, or on the surface of agar, or as monolayers on the bottom of shallow dishes. Classical cell culture technology is carried out in nutrient mixtures with cells usually cultured as a monolayer attached to a hydrophilic surface, commonly, sterile treated polystyrene.

Some types of investigations lend themselves to studies with whole cells and inevitably require cell culture techniques as an essential step in the investigation. In addition, the cells are usually radiolabeled either by incorporation of the radiolabel into the cell or through some type of interaction with a site on the cell surface. A number of assays and methodologies exist for identifying and/or quantitating antigens (i.e., proteins, nucleic acids, etc.) that exist or in cells, bacteria or viruses. However, these assays involve measurements of static systems not dynamic, i.e., living, systems which are responding to a stimulus. An example of measurements involving static systems is illustrated by Czerkinsky, 1.2 Antigen-secreting Cells, Methods of Enzymatic Analysis, 3d ed., Vol. X, Antigens and Antibodies 1, Bergmeyer (Ed.-in-chief) (1986).

WO 94/26413 published on Nov. 24, 1994 describes an apparatus and method for studying cellular processes utilizing a vessel having a base including a layer comprising a scintillant substance and which is adapted for attachment and/or growth of cells. Cellular processes are examined by scintillation proximity assay using a reagent labeled with a radioisotope under conditions which cause a portion of the labelled reagent to become associated with or released from the cells adhering to the layer.

Adams et al., Nature, Vol. 349, pages 694–697 (Feb. 21, 1991) describes fluorescence ratio imaging of cyclic AMP in single cells. The change in shape of the fluorescence emission spectrum allows cAMP concentrations and the activation of the kinase to be nondestructively visualized in single living cells microinjected with the labelled holoenzyme. Thus, the label is incorporated into the cell.

U.S. Pat. No. 4,626,513, issued to Burton et al. on Dec. 2, 1986, describes a process and apparatus capable of performing radioassays on a continuous basis. A chamber is provided containing a quenching solution, a plurality of ligand molecules and a plurality of receptor molecules. The ligand molecules form a free species labelled with a beta particle emitter while the receptor is immobilized on a solid support such as the chamber wall or a microbead within the chamber. Ligand introduced with the sample competes with ligand molecules already in the chamber for receptor sites on the receptor molecules and the free species is allowed to diffuse about the chamber. A beta particle detector in communication with the chamber at a fixed position detects only those beta particles emitted from within the quenching distance of the quenching solution. The quenching properties of the solution are used in place of the conventional separation step. The process and apparatus are easily adapted for continuous monitoring of ligand level and is well suited for radioimmunoassays. There is no mention of any application with respect to a solid phase cell-based assay.

U.S. Pat. No. 4,000,252, issued to Kosak on Dec. 28, 1976, describes an immunoassay system which utilizes particles or other structures such as tube walls into which are embedded a fluorescer and which are coated with a ligand. In the preferred embodiment of Kosak, radiolabelled antigen and unlabelled antigen compete for binding to the ligand which is coated on the scintillant support structure. Kosak discloses that upon binding of the radiolabelled antigen to the ligand, the scintillant emits light which is measured by a photomultiplier. There is no mention of any application with respect to a competitive solid phase cell-based assay.

Langer et al., Circulation Research, Vol. 24, No. 5, pages 589–597 (May 1969), describes a preparation of a single layer of contractile myocardial cells on the surface of a slide composed of glass scintillator material and a method for analysis of $Ca^{2+}$ exchange in these cells by direct, continuous counting of cellular radioactivity.

Frank et al., Circulation Research, Vol. 41, No.4, pages 702–714 (September 1977), describes a technique for measuring cellular isotopic exchange which was monitored by scintillation-disk flow cell technique. This method involves the growth of a cellular monolayer on one surface of each of two disks composed of polystyrene combined with scintillator material.

U.S. Pat. No. 4,568,649, issued to Bertoglio-Matte on Feb. 4, 1986, describes ligand detection systems which employ scintillation counting. The method utilizes support particles coated with ligand and impregnated with a fluorescer. When these particles are placed in an aqueous medium which contains the binding partner for the ligand in radiolabelled form, binding of the binding partner to the ligand is detected by the emission of light energy (i.e., scintillation). The system is designed such that when the ligand and its binding partner are not bound to one another, the radiolabelled moiety is too far removed from the fluorescer to cause activation of the fluorescer. When the radiolabelled binding partner is bound to the ligand coated on the surface of the fluorescer particles, activation of the fluorescer occurs and light energy is emitted.

PCT International Application having Publication Number WO 90/03844, published Apr. 19, 1990, describes a microtitre well plate intended for binding assays. Application for cell-based assays is not described.

European Patent Application Publication Number 0 378 059 published Jul. 18, 1990 describes a fibrous support for scintillation proximity assays to detect a radiolabelled reactant in a liquid sample.

SUMMARY OF THE INVENTION

In one embodiment the present invention concerns a competitive solid phase cell-based assay which comprises:

a) reacting unlabeled analyte produced by at least one unlabeled cell in response to a stimulus, wherein the cell is not attached to the solid phase, with
   (i) a capture reagent specific for the analyte to be assayed, said capture reagent being immobilized on the solid phase; and
   (ii) labeled analyte wherein said labeled analyte competes with unlabeled analyte for the capture reagent; and b) detecting and/or quantitating the amount of labeled analyte which has bound the capture reagent.

In another embodiment, this invention concerns a solid phase cell-based assay which comprises:

(a) reacting (i) unlabeled analyte produced by at least one unlabeled cell in response to a stimulus, wherein the cell is not attached to the solid phase, with (ii) a captare reagent specific for the analyte to be assayed, said capture reagent being immobilized on the solid phase and (iii) a detector reagent which specifically binds with the unlabeled analyte at a site different from the site where the capture reagent binds; and (b) detecting and/or quantitating the amount of analyte produced by the cell from the signal generated in step (a).

DETAILED DESCRIPTION OF THE INVENTION

One of the unique features of this invention is the ability to study cellular and biochemical processes in living cells which are responding to a stimulus by evaluating cell-related analytes (i) without the need to attach the cell to the solid phase, (ii) without the need to employ cell culture techniques and (ii) without the need to radioactively label the cell either by incorporating a radioactive label into the cell or by introducing a radioactive label onto the cell surface. Unlabeled analyte produced by the unlabeled cell in response to a stimulus can be detected utilizing a competitive format in which labeled analyte competes with unlabeled analyte for binding with the capture reagent.

Unlabeled analyte produced by the unlabeled cell in response to a stimulus can also be detected utilizing a sandwich format in which the unlabeled analyte binds with both a capture reagent and a detector reagent. The reaction of the capture reagent, analyte and detector reagent can be sequential or simultaneous. The resulting capture reagent—unlabeled analyte—detector reagent complex is detected using techniques well known to those skilled in the art.

The advantages of the present invention include elimination of the need for a separate culturing step which is considered "heresy" by cell culture purists. However, as the examples described below show, the cell or cells respond to stimulation without media present or the need to grow the cells in the plate. This saves at least a day or more in time and labor. Because all cells are used in the well, a smaller amount is needed. Furthermore, the cells do not need to be attached to the solid phase to be assayed. Since it is a one-well assay, the number of steps are reduced and extractions are eliminated. The detection method is independent of the cell. Thus, the cell itself is not labeled. The detection method can be radiometric or non-radiometric.

The competitive solid phase cell-based assay comprises:

a) reacting unlabeled analyte produced by at least one unlabeled cell in response to a stimulus, wherein the cell is not attached to the solid phase,
   (i) a capture reagent specific for the analyte to be assayed, said capture reagent being immobilized on the solid phase; and
   (ii) labeled analyte wherein said labeled analyte competes with unlabeled analyte for the capture reagent; and b) detecting and/or quantitating the amount of labeled analyte which has bound the capture reagent.

In another embodiment the invention concerns a sandwich solid phase cell-based assay which comprises:

(a) reacting (i) unlabeled analyte produced by at least one unlabeled cell in response to a stimulus, wherein the cell is not attached to the solid phase, with (ii) a capture reagent specific for the analyte to be assayed, said capture reagent being mobilized on the solid phase and (iii) a detector reagent which specifically binds with the unlabeled analyte at a site different from the site where the capture reagent binds; and (b) detecting and/or quantitating the mount of analyte produced by the cell from the signal generated in step (a).

Living cells have the capacity to respond metabolically to environment changes in pH, chemicals, biochemicals, light, etc. Many of these responses are cascades of intracellular reactions which can include second messenger synthesis, calcium ion flux, phosphorylation or dephosphorylation events, DNA synthesis, transcription of DNA and translation of mRNA to result in protein synthesis. For example, hematopoietic colony stimulating factors are a group of glycoproteins which stimulate hemopoietic cells to proliferate, differentiate and become activated (D. Metcalf, *Blood* 67 (1986) 257–267). Tissues or cells in culture can be shown to increase or decrease the amount of intracellular cAMP as a result of activation or deactivation of the enzyme adenylate cyclase in response to exposure to hormones or neurotransmitters (Y. Salomon, *Methods of Enzymology* 195 (1991) 22–28). Cell lines not normally responsive to hormones, peptides or cytokines can be made responsive by expression of the appropriate cloned receptors (C. W. Liaw, et al., *Endocrinology* 137 (1996) 72–77).

Thus, virtually any type of cell-related analyte produced by at least one unlabeled cell in response to a stimulus can be studied using the present invention. Examples of suitable analytes include, but are not limited to, receptor ligands, protein and lipid metabolite precursors, such as amino acids and fatty acids, cyclic nucleotides such as cyclic AMP, leukotrienes, cytokines, growth factors, nucleic acids and enzymes. Basically, living cells are stimulated using, for example, chemical stimulation, ligand stimulation or any other means of stimulating cells known to those skilled in the art, so that analytes produced by the cell can be evaluated. However, detection of the cell-related analyte produced in response to the stimulus is made independently of the cell.

Solid phase supports suitable for practicing the invention include synthetic polymer supports such as polystyrene, polypropylene, substituted polystyrene, e.g., aminated or carboxylated polystyrene; polyacrylamides; polyamides; polyvinylchloride, etc.; glass beads; agarose; nitrocelullose; nylon; polyvinylidenedifluoride; surface-modified nylon, etc. The preferred support is a multiwell plate such as a microlitre plate.

The capture reagent and the detector reagents can be any reagents which are specific for the analyte being assayed provided that the capture reagent and the detector reagent bind to the analyte at different sites. Examples of suitable capture and detector reagents include, but are not limited to, members of specific binding pairs which can be of the immune or non-immune type. Immune specific binding pairs are exemplified by antigen/antibody systems or hapten/anti-hapten systems. The antibody member of the binding pair, whether polyclonal or monoclonal or an immunoreactive fragment thereof, can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the difulfide bonds connecting the heavy chain components of the intact antibody. If the antigen member of the specific binding pair is not immunogenic, e.g., a hapten, it can be covalently coupled to a carrier protein to render it irnmunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc.

The capture reagent can be immobilized directly or indirectly, covalently or non-covalently on the solid phase using methods well known to those skilled in the art. An example of direct immobilization is coating the capture reagent onto the solid phase.

In the competitive assay format, labeled analyte which competes with unlabeled analyte for binding with the capture reagent can be labeled with a component of a reporting system or a member of a specific binding pair. The term "reporting system" is discussed below.

Any type of sandwich assay format can be used to practice the invention. For example, the reaction of the capture reagent, analyte and detector reagent can be sequential or simultaneous. The detector reagent should be capable of binding unlabeled analyte at a site different from the site bound by the capture reagent. Examples of suitable detector reagents are discussed above.

The detector reagent or labeled analyte can be labeled directly or indirectly, covalently or noncovalently, with a component of a reporting system or a member of a specific binding pair using conventional techniques well known to those skilled in the art. The term "reporting system" as used herein refers to the reporter selected and any means of linking the reporter to the detector reagent or labeled analyte or to a member of a specific binding pair. Type of specific binding pairs are discussed above. For example, the detector reagent can be linked to a reporter such as an enzyme or a radioisotope or it can be linked to a member of a specific binding pair such as biotin and the biotinylated detector reagent could then be detected by reacting it with a labeled avidin or streptavidin. Thus, a reporter can be linked directly or indirectly, covalently or noncovalently, to the detector reagent, labeled analyte or member of a specific binding pair. Reporters can be radioactive isotopes, enzymes, fluorogenic, colorimetric, magnetic, chemiluminescent or electrochemical materials or a first member of a specific binding pair.

In addition, detection of the reporter can be made directly or indirectly. For example, if the detector reagent was an antibody then it could be labeled with fluorescein which can be detected directly or indirectly. In the case of direct detection, fluorescence would be detected directly. In the case of indirect detection, fluorescein can be detected using a labeled anti-fluorescein antibody. The label on the anti-fluorescein antibody would then be detected.

If the reporter used to label analyte or the detector reagent is an enzyme, then the detector signal can be amplified by using catalyzed reporter deposition technology as described in U.S. Pat. No. 5, 196,306, the discussion of which is hereby incorporated by reference. In catalyzed reporter deposition, an analyte dependent enzyme activation system comprising at least one enzyme is reacted with a conjugate consisting of a detectably labeled substrate specific for the enzyme system, the conjugate reacts with the analyte dependent enzyme activation system to produce an activated conjugate which deposits substantially wherever receptor for the activated conjugate is immobilized, said receptor not being reactive with the analyte dependent enzyme activation system wherein deposited detectable labels either directly or indirectly generate a signal which can be detected or quantitated.

For example, if analyte or detector reagent was labeled with the enzyme, horseradish peroxidase, then after the enzyme-labeled analyte bound with the capture reagent, it could then be reacted with a conjugate such as biotin tyramine. The conjugate would be activated and the activated biotin tyramine would deposit wherever there was receptor for the activated conjugate. The deposited biotin could then be detected through reaction with a labeled streptavidin or labeled avidin.

The following examples are intended to illustrate the invention.

EXAMPLE 1

Adenylate Cyclase FlashPlate® Assay

Cells (HEK293 (ATCC) with a cloned CRF2 receptor) were harvested from tissue calmre flasks using Vetserie EDTA (GIBCO). The cells were pelleted by centfifuging for 5 minutes at 1000 xg at room temperature. The pellet was resuspended in stimulation buffer (1X Phosphate Buffered Saline (PBS), 0.1% Bovine Serum Albumin (BSA), 500 µM 3-Isobutyl-1-methylxanthine CIBMX), 0.09% 2-ehloroacetamide), washed by centrifugation for 5 minutes at 1000 xg at room temperature. The pellet was resuspended in stimulation buffer to a concentration of $1\times10^6$ cells/mL.

Fifty microliters of cells were then added to a FlashPlate® (DuPont) well that had been previously coated with anti-cAMP antibody (DuPont) (Sheep anti-rabbit antibody (DuPont) was coated overnight, blocked with 1% BSA then coated with rabbit anti-cAMP antibody). A set of cAMP standards were prepared in the stimulated buffer used for the cells to concentrations of 0, 10, 25, 50, 100, 250, 500, and 1000 pmol/mL by diluting down to the appropriate concentration from a stock standard of 5000 pmol/mL (DuPont). Fifty microliters of standards were added to the FlashPlate® wells. The cells were then stimulated with a chemical agohist (Forskolin) (Sigma) at concentrations of 0, 15.6, 31.2, 62.5, 125, 250, 500, and 1000 μM or a ligand to a receptor on the cell membrane (Sauvagine is a ligand for the corticotropin releasing factor 2 receptor) (Penzinsula Labs) at concentration of 0, 12.5, 25, 50, 100, 200, 400, and 800 nM which then activates adenylate cyclase to produce cAMP. After stimulation, the detection mix (13.6% acetic acid, sodium salt trihydrate, 0.6% EDTA disodium salt, 0.09% sodium azide, 10 mM calcium chloride, and 0.35% TRITON X-100(t-octylphenoxypolyethoxyethanol) containing an $^{125}$I labeled cAMP tracer (DuPont) was added to the well. The cAMP that was produced by the stimulated cells then competed, with the $^{125}$I labeled cAMP for binding to the FlashPlate® through the anti-cAMP antibody. After twenty four hours at room temperature the FlashPlate® was read for counts per minute bound to each well on a Top-Count™ scintillation counter (Packard). The sample values were interpolated from the standard curve.

Results are presented in the following Tables. Table 1 shows the Forskolin stimulation and Table 2 shows the ligand stimulation. The negative control for both assays was the cells not stimulated. For both types of stimulation the assay showed a significant increase in cAMP produced and detected for the stimulated cells and not for unstimulated cells.

TABLE 1

Chemical Stimulation

| Forskolin (μM) | Stimulated Cells cAMP | Unstimulated Cells (pmol/mL) |
|---|---|---|
| 1000 | 1191 | 21 |
| 500 | 818 | 9 |
| 250 | 617 | 8 |
| 125 | 381 | 2 |
| 62.5 | 169 | 3 |
| 31.2 | 101 | 2 |
| 15.6 | 55 | 3 |
| 0 | 13 | 3 |

TABLE 2

Ligand Stimulation

| Sauvagine (nM) | Stimulated Cells cAMP | Unstimulated Cells (pmol/mL) |
|---|---|---|
| 800 | 325 | 12 |
| 400 | 295 | 6 |
| 200 | 207 | 2 |
| 100 | 135 | 1 |
| 50 | 78 | 0 |
| 25 |  | 2 |
| 12.5 | 33 | 0 |
| 0 | 20 | 0 |

EXAMPLE 2

Leukotriene $C_4$ FlashPlate® Assay

Whole blood (30 mL) from a human donor was collected in a heparinized syringe. The leukocytes were separated from the whole blood by lysing 0.1 mL whole blood with 1.0 mL of a red blood cell lysing reagent (0.168M $NH_4Cl$, 0.01M $KHCO_3$, 0.1 mM EDTA). After 10 minutes at room temperature the leukocytes were pelleted by high speed centrifugation (10 seconds at 14,000 xg). The pellet was resuspended in PBS and washed by centrifugation. The pellet was resuspended in PBS containing calcium chloride and magnesium chloride. The cells were serially diluted in the PBS to evaluate different concentrations of cells. $LTC_4$ standards (DuPont) were prepared in the PBS to concentrations of 0, 0.025, 0.05, 0.1, 0.2, 0.4, 0.8, and 1.6 ng/0.1 mL. The cells and the standards (0.1 mL) were added to the FlashPlate® (DuPont) that had been previously coated with sheep anti-rabbit antibody (DuPont), blocked, and then coated with rabbit antiLTC$_4$ antibody (DuPont). The cells were either stimulated with calcium ionophore A23187 (10 μL of a 2 μM stock) (Sigma) to produce $LTC_4$ or as a negative control, water (10 μL) was added to the cells. After stimulation 0.1 mL of detection mix ($^3$H-LTC$_4$ tracer (DuPont) was added to 0.9% NaCl, 0.1% gelatin, 0.01M EDTA, 0.1% sodium azide in 10 mM phosphate buffer) was added to the well. The $LTC_4$ that was produced by the stimulated cells then competed with the $^3$H labeled $LTC_4$ for binding to the FlashPlate® through the anti-$LTC_4$ antibody. After ten minutes at 4° C. the FlashPlate® was read for counts per minute bound to each well on a TopCount™ scintillation counter. The sample values were interpolated from the standard curve.

Results are presented in Table 3. Table 3 shows that the Calcium Ionophor A23187 stimulated cells produced more $LTC_4$ than the unstimulated cells and that the $LTC_4$ was able to be detected by this method.

TABLE 3

| # Cells/μL | Stimulated Cells LTC$_4$ | Unstimulated Cells (ng/0.1 mL) |
|---|---|---|
| 5000 | 5.18 | 1.94 |
| 2500 | 1.94 | 1.18 |
| 1250 | 0.41 | 0.09 |
| 0 | 0 | 0 |

What is claimed is:

1. A competitive solid phase one-well cell-based assay which comprises:
   (a) subjecting at least one unlabeled cell to a stimulus to cause said at least one cell to produce an unlabeled analyte, wherein said at least one cell need not be attached to the solid phase;
   (b) reacting the unlabeled analyte produced in step (a) with
      (i) a capture reagent specific for the analyte to be assayed, said capture reagent being immobilized on the solid phase; and
      (ii) labeled analyte, wherein said labeled anayte competes with unlabeled analyte for the capture reagent; and
   (c) detecting and/or quantitating the amount of labeled analyte which has bound the capture reagent, wherein said subjecting, reacting and detecting and/or quantitating are performed within a single well.

2. An assay according to claim 1 wherein the capture reagent is a member of a specific binding pair.

3. An assay according to claim 1 wherein the analyte is selected from the group consisting of cyclic nucleotides, leukotrienes, cytokines, growth factors, nucleic acids, and enzymes.

4. An assay according to claim 1 wherein the label on the labeled analyte is selected from the group consisting of enzymes, radioactive isotopes, fluorogenic, colorimetric, chemiluminescent, or electrochemical materials.

* * * * *